(12) United States Patent
Mikus et al.

(10) Patent No.: US 10,842,587 B2
(45) Date of Patent: Nov. 24, 2020

(54) METHOD FOR MINIMALLY INVASIVE SURGERY USING THERAPEUTIC ULTRASOUND TO TREAT SPINE AND ORTHOPEDIC DISEASES, INJURIES AND DEFORMITIES

(71) Applicant: MISONIX, INCORPORATED, Farmingdale, NY (US)

(72) Inventors: Paul Mikus, Coto de Caza, CA (US); Dan Voic, Cedar Grove, NJ (US); Alexander Darian, Brightwaters, NY (US); Scott Isola, Deer Park, NY (US); Christine Moley, Monroe, NY (US)

(73) Assignee: MISONIX, INCORPORATED, Farmingdale, NY (US)

( * ) Notice: Subject to any disclaimer, the term of this patent is extended or adjusted under 35 U.S.C. 154(b) by 1295 days.

(21) Appl. No.: 14/939,668

(22) Filed: Nov. 12, 2015

(65) Prior Publication Data

US 2016/0129285 A1    May 12, 2016

Related U.S. Application Data

(60) Provisional application No. 62/078,727, filed on Nov. 12, 2014.

(51) Int. Cl.
*A61B 90/13* (2016.01)
*A61B 17/32* (2006.01)

(52) U.S. Cl.
CPC .... *A61B 90/13* (2016.02); *A61B 2017/32007* (2017.08); *A61B 2017/320082* (2017.08)

(58) Field of Classification Search
CPC ...................................................... A61N 7/00
See application file for complete search history.

(56) References Cited

U.S. PATENT DOCUMENTS

| 5,651,783 A * | 7/1997 | Reynard ............... A61B 1/042 606/17 |
| 2010/0312312 A1* | 12/2010 | Jones ..................... A61N 5/062 607/88 |
| 2015/0011888 A1* | 1/2015 | Akagane .......... A61B 17/32006 600/459 |

* cited by examiner

*Primary Examiner* — Hien N Nguyen
(74) *Attorney, Agent, or Firm* — R. Neil Sudol; Henry D. Coleman (57) ABSTRACT

A method for minimally invasive surgery using therapeutic ultrasound in spine and orthopedic orthopedic procedures. The method includes a minimally invasive access port, a therapeutic ultrasound probe to treat a targeted area through the port, and a protective sheath that enables application of the therapeutic ultrasound without causing unintended tissue damage.

2 Claims, 6 Drawing Sheets

METHOD FOR MINIMALLY INVASIVE SURGERY USING THERAPEUTIC ULTRASOUND TO TREAT SPINE AND ORTHOPEDIC DISEASES, INJURIES AND DEFORMITIES

BACKGROUND OF THE INVENTION

Therapeutic Ultrasound holds many advantages in its use as a tissue removal and treatment tool over existing surgical modalities. Currently, therapeutic ultrasound is used for many different types of tissue interaction. One type of use of therapeutic ultrasound is to cut or remove tissue in a precise manner while limiting blood loss and thermal damage. This type of clinical application has become popular in spine and orthopedic procedures as a replacement to curette, bone drills and saws. The use of therapeutic ultrasound devices in procedures to remove bone for example has lead to more precise bone removal while reducing the potential for soft tissue injury (Sanborn, 2011). Thus the advantage of currently developed therapeutic ultrasound applications for tissue removal is the precision it affords the surgeon while increasing safety in a procedure.

The recent trend is surgical procedures is towards less invasive access to surgical sites in order to improve recovery times for the patient. The less or minimally invasive access to surgical sites often involves navigating through existing anatomical structures without causing damage to those structures. For example, companies like Nuvasive, Medtronic and Depuy have pioneered lateral and transforaminal access with a variety of different tuba access ports and expandable retractors that enable treatment of the spine without the need for open surgical techniques. The result is spine surgery that replaces cutting through layers of muscle to access the spine, with newer techniques for access to the surgical site by changing the angle of introduction to allow muscles to be moved aside rather than cut. This new type of minimally invasive approach to the surgical sites inside the body has reduced the operating area for surgical tools to perform their function. Compared to an open surgical procedures, minimally invasive approaches have very tightly confined spaces that are surrounded by normal body cavity functions around the targeted treatment area.

Therapeutic ultrasound devices that are designed for use in removing bone are generally meant to deliver a sufficient amount of ultrasonic vibratory power at the tip of the applicator sufficient to cause bone removal in a precise and safe manner. The safety of the bone cutting element has revolutionized spine and orthopedic procedures because it can cut hard tissue without effecting soft tissue. The advent of minimally invasive procedures has created a need to protect against unintended tissue damage along the transmission pathway of ultrasound energy to the bone cutting applicator tip. Typically, the transmission of that vibratory power occurs from the hand-piece which houses the transducers that convert the electrical signal to a mechanical function through the horn to an applicator tip to be applied to the treatment site. The transmission along the pathway from the ultrasonic transducer to the applicator tip is necessary in order to cause the desired effect in the targeted tissue. Yet the transmission of the vibratory energy can create unique challenges in the use of the device during surgery. For example, if a surgeon where to touch the device along the transmission path of the vibratory energy they would run the risk of the vibratory energy causing unintended damage to their skin at the point of contact. In order to protect against this in open surgery, most therapeutic ultrasound devices employ hand-pieces that provide a place to hold the device and guard against incidental contact with the vibratory transmission path. These methods have been effective if designed properly in creating protection in generally open spaces from causing unintended damage along most of the transmission path. In minimally invasive procedures, the means to protect holding the probe is made difficult because the holding of the probe must be done in a way that allows for maximum control of the probe while not impeding the reduced visual field in through the minimally invasive access port. Thus a means to allow for holding a probe with one or two hands and not impeding visualization of the targeted treatment site while avoiding unintended tissue damage to the surgeon's hands would be desirable.

When therapeutic ultrasound probes are energized, the transmission of vibratory energy at power levels sufficient to cause removal of hard tissues like bone can also result in a rise in temperature. Typically losses of the energy along the transmission path are minimal and the pathways themselves are designed for optimal transmission so that minimal thermal build up occurs alone the path. At the applicator site where the energy is transferred to the targeted treatment site, the vibratory energy can cause a rise in temperature that results in thermal damage in addition to the mechanical disruption of the targeted treatment site. This thermal damage is undesirable and an unintended result of the application of vibratory energy.

A strategy to minimize the thermal rise at the applicator site is to cool it with a flow of liquid over the applicator during operation. For example, Novak (Novak, 2002) describes a method for cooling an ultrasonic cutting blade by the distribution of fluid. This type of approach has proven beneficial in open surgical procedures because the cooling fluid facilitating the removal of the heat build up such that it does not have a chance to reach temperatures that can cause tissue necrosis mitigates the rise in temperature. The fluid is allowed to flow into the open surgical field, or can be evacuated occasionally by aspiration separately or incorporated into the probe. This strategy is limited to applications where there is enough room to flow a sufficient quantity of fluid to control the thermal buildup. This strategy does not mitigate against the potential for thermal damage along the entire transmission pathway of the vibratory energy. Nor does it mitigate against accidental contact with points along the pathway.

What does not exist but would be beneficial for applying therapeutic ultrasound for the removal of tissue in minimally invasive approaches is a method and device to protect against unintended damage to the surrounding tissue along the access pathway or the targeted treatment site.

SUMMARY OF THE INVENTION

Described herein are a method and device for enabling minimally invasive use of therapeutic ultrasound for the removal of tissue at the targeted treatment site while protecting against unintended damage along the transmission path of ultrasonic vibratory energy to the applicator tip or probe head. The unique aspects of this method and design include a novel thermal insulation sheath to prevent unintended damage in a confined space. Another unique aspect of this method and approach is the use of an expandable sheath that creates a physical space between the vibratory transmission pathway and the surrounding non targeted tissue along a pathway to the treatment site.

DETAILED DESCRIPTION

We describe a method and device for enabling minimally invasive use of therapeutic ultrasound for the removal of tissue at the targeted treatment site while protecting against unintended damage along the ultrasonic vibratory transmission of energy to the applicator tip. The unique aspects of this method and design include a novel thermal insulation sheath to prevent unintended damage in a confined space. Another unique aspect of this method and approach is the use of an expandable sheath that creates a physical space between the vibratory transmission pathway and the surrounding non-targeted tissue along a pathway to the treatment site.

Another unique aspect of this method is a novel sheath design that extends the handle without impeding visualization of the target treatment field. Another unique aspect of this method is the incorporation of the sheath into the access device to protect against transmission of energy through the access device and causing unintended tissue damage. Another unique aspect of this method is the incorporation of elements into the protective sheath that improves visualization at the treatment site by illuminating it, or irrigating or suctioning debris away.

In a preferred embodiment a method to apply therapeutic ultrasound for removal of tissue in a minimally invasive approach uses an ultrasound hand-piece that houses the transducer that translates the electrical signal to a mechanical wave. The ultrasound wave is transmitted along a horn to the applicator tip to cause tissue removal. The horn and applicator tip are housed in a sheath to allow the introduction of the assembly into a minimally invasive access port. The sheath is in a closed position creating the smallest profile during the introduction and placement of the probe at the targeted treatment site. Once the probe is positioned at the treatment site, the sheath can be expanded so that the surrounding tissue is spaced at a distance sufficient enough to ensure no direct contact or ultrasound vibratory or thermal energy transmission along the shaft in quantities that can cause unintended damage. Once the application of the energy to the targeted treatment sit has been completed, the sheath can be collapsed allowing for easy removal of the probe from the minimally invasive access port. In another embodiment the expandable sheath is the minimally invasive access port and allows for an exchange of therapeutic ultrasound tools in the retractable sheath. The retractable sheath can be used for therapeutic ultrasound probes and other tools necessary for a minimally invasive surgical procedure.

Figure 1:
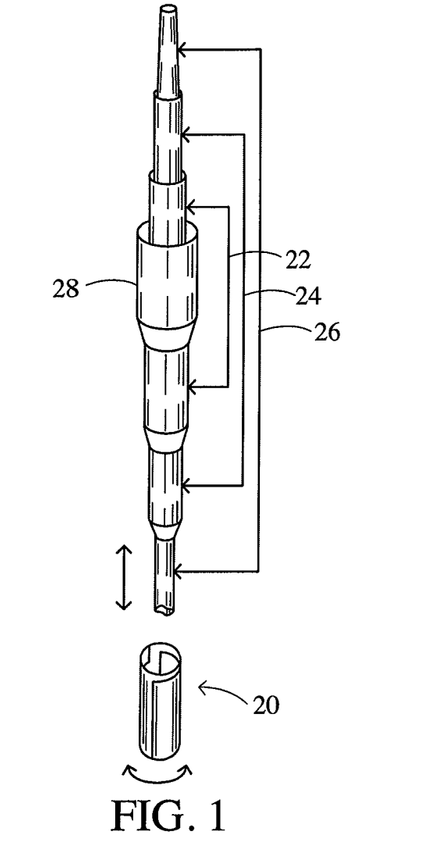
FIG. 1 is a schematic perspective view of a sheath or surgical port device in accordance with the present invention, showing a dilation assembly to expand the sheath.
Figure 2:
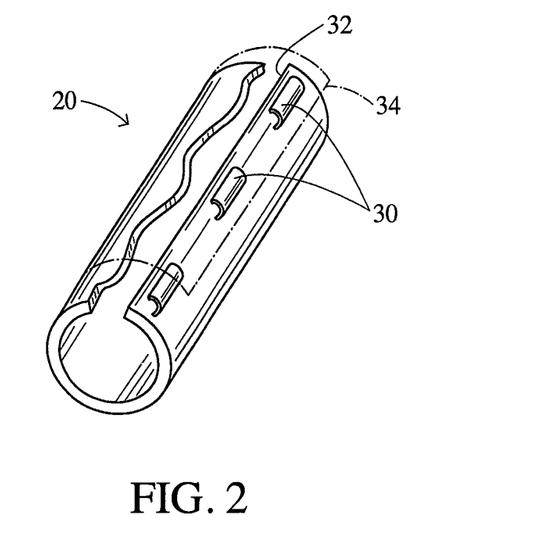
FIG. 2 is a schematic perspective view, on a larger scale and partially broken away, of the sheath or port device of FIG. 1.

As depicted in FIG. 1, an alternately expandable and collapsible sheath or tubular port member 20 takes the collapsed form of a spiral web or sheet that by virtue of internal spring forces has a shape memory tending to maintain the sheath or port member in a collapsed spiraling configuration. Once an incision is made in a patient's skin and underlying connective or muscle tissues, as in a spinal operation, a distal end portion of the collapsed sheath or port member 20 is inserted into the incision. The sheath or port member 20 is then expanded, for instance, by a step-wise insertion of a number of expander sleeves 22, 24, 26, 28 of ever increasing diameter. As depicted in FIG. 2, sheath or port member 20 is formed with a plurality of hooks 30 in a linear array along a longitudinal inner edge 32 that serve to receive and catch an opposing outer longitudinal edge 34 and thereby lock the tubular sheath to port member in an expanded use configuration. After termination of a procedure during which a surgical instrument such as an ultrasonic bone cutting blade (see, e.g., U.S. Pat. No. 6,379,371) is used to operate on tissues at a surgical site surrounded by the expanded sheath or port member 20, forceps or pliers may be used to remove external edge 34 from hooks 30, releasing the sheath or port member 20 and allowing it to contract back to its collapsed configuration under internal shape memory forces. It is to be noted that sheath or port member may act as a retractor, maintaining the incision in a suitably open configuration, or alternatively may be inserted inside a retractor which remains in place to hold the incision tissues apart. In the latter case the expanded sheath 20 may be entrained to the inserted instrument and form, together with an outer surface of the instrument shaft or probe, an annular channel that may be connected to a suction source for the evacuation of irrigant and organic debris from the surgical site.

Figure 3:
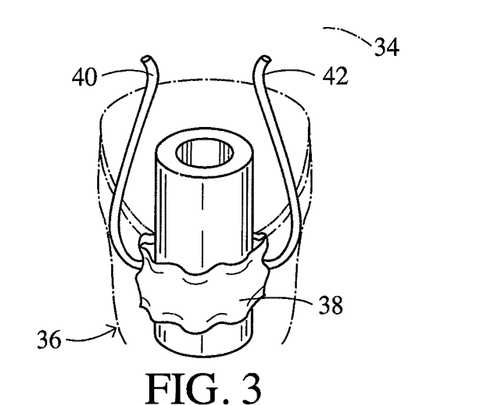
FIG. 3 is a schematic perspective view of another sheath or surgical port device in accordance with the present invention, showing a balloon collar in a collapsed configuration.
Figure 4:
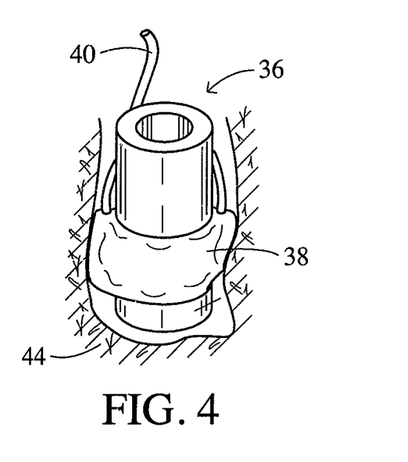
FIG. 4 is a schematic perspective view of the sheath or port device of FIG. 3, showing the balloon in an expanded configuration inside an incision in organic tissue.

In another embodiment shown in FIGS. 3 and 4, an expandable sheath 36 is a substantially rigid tubular member provided with an expandable balloon 38 on the outer surface (not separately designated) of the sheath to provide a spacing between the probe and the surrounding tissue. FIG. 3 shows balloon 38 in a deflated insertion configuration. Upon injection of fluid such as air or an aqueous solution from a pressurized source (not shown) into balloon 38 via a tubular conduit 40, balloon 38 expands to an inflated configuration as shown in FIG. 4. Optionally, a second tubular conduit 42 may extend to balloon 38 for enabling a circulation of the fluid for cooling purposes. As sheath 36 is frictionally wedded to tissues 44 along the walls of an incision (not separately designated) sheath 36 is functionally a port member and may perform as a retractor. When any sheath disclosed herein is utilized as a port member or retractor, it has a large enough diameter (several centimeters typically) to enable both the insertion of a surgical instrument and a visual of the instrument tip or operative hear and the tissues at the surgical site. As a port member sheath 36 or 20 typically has a length of 5 to 10 centimeters, particularly where used in minimally invasive spinal or orthopedic surgery.

Figure 5:
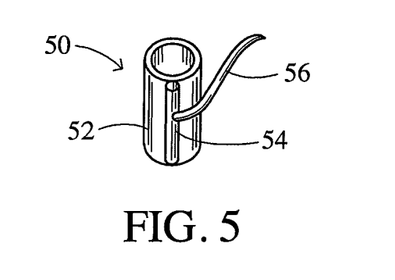
FIG. 5 is a schematic perspective view of a further sheath or surgical port device in accordance with the present invention, showing a balloon insert in a collapsed configuration.
Figure 6:
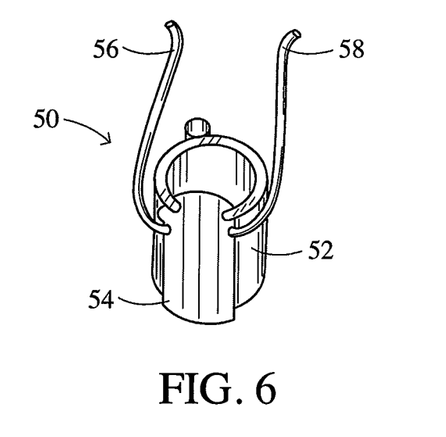
FIG. 6 is a schematic perspective view of the sheath or port device of FIG. 5, showing the balloon in an expanded configuration.

As shown in FIGS. 5 and 6, a sheath or port member 50 includes a longitudinally slotted sleeve 52 that is provided in a longitudinal slot (not designated) with a balloon or bladder 54. Sleeve 52 has an internal spring bias or shape memory that tends to maintain the slot in a minimal or narrow size. Pumping of fluid into balloon or bladder 54 via a tubular hose 56 causes the balloon or bladder to expand from a deflated insertion configuration (FIG. 5) to an expanded use configuration (FIG. 6) whereby sleeve 52 is pushed open to a larger diameter. Where the expanded balloon or bladder 54 is placed into contact with tissues of a patient and may come into extended contact with a vibrating probe surface, a second hose 58 may be provided to enable a circulating of the expansion fluid for cooling purposes.

In another embodiment, the expandable sheath opens just at the tip to expose the applicator so that the energy can be applied without damage to the surround non-targeted tissue. The sheath can partially open, exposing just a front facing direction of the probe, protecting tissue that is below the probe and not part of the target treatment area.

Figure 7:
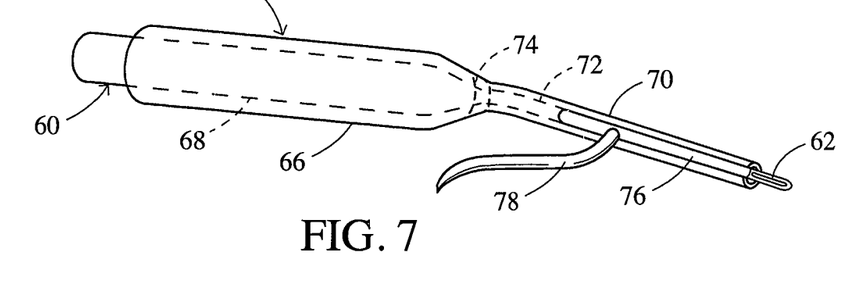
FIG. 7 is a schematic perspective view of an ultrasonic instrument assembly with a sheath having an expander balloon in accordance with the invention.

As illustrated in FIG. 7, a surgical instrument 60 with an applicator tip or probe head 62 (such as a bone cutting blade) longitudinally traverses an elongate sheath 64. Sheath 64 has a large-diameter proximal end portion 66 that accommodates a larger part of the instrument such as a handpiece 68 and further has a small-diameter distal end portion 70 which surrounds a shaft or horn 72 of the instrument. End portions 66 and 70 are inclined relative to one another and are connected by a flexible coupling 74 such as a living hinge or a ball joint to enable insertion of the instrument 60, where handpiece 68 and shaft or horn 72 are rigid with one another.

Sheath 64 and particularly distal end portion 70 thereof has a slot (not separately shown) that is occupied by a balloon 76 that is alternatively expandable and collapsible via a hose 78 as described hereinabove with reference to FIGS. 5 and 6.

In another embodiment the expandable sheath opens once the probe is positioned at or near the targeted treatment site. When the sheath is expanded it creates room for the probe to move within the expanded sheath without the need to reposition the probe because it floats in the space created by the expansion.

Any of the sheaths or port elements disclosed herein, for instance, 20, 36, 50, may be configured to incorporate a suction function for removal of irrigant, tissue fragments and surgical debris at the targeted treatment site. The suction may be distributed in the walls of the sheath to additionally act as a thermal insulation to avoid unintended tissue damage by the probe in a confined treatment space. The sheath suction space and moving fluid therein acts as an insulator and a means for convection removal of any thermal build up due to the tightly confined spaces in a minimally invasive application of therapeutic ultrasound. A surgical probe that is used in conjunction with a sheath or port element as described herein may incorporate a fluid delivery line that delivers fluid to the applicator tip or probe head. The fluid delivery during the therapeutic ultrasound application reduces thermal build up. The suction feature built into the sheath or port element evacuates the fluid with the debris and tissue. The combination of fluid delivery and suction removal through the sheath create insulation from thermal damage to the surrounding non-targeted tissue. The fluid and suction in the sheath act by conducting away any thermal build up from the probe and or applicator so that temperatures do not reach thermal damage levels.

Figure 8:
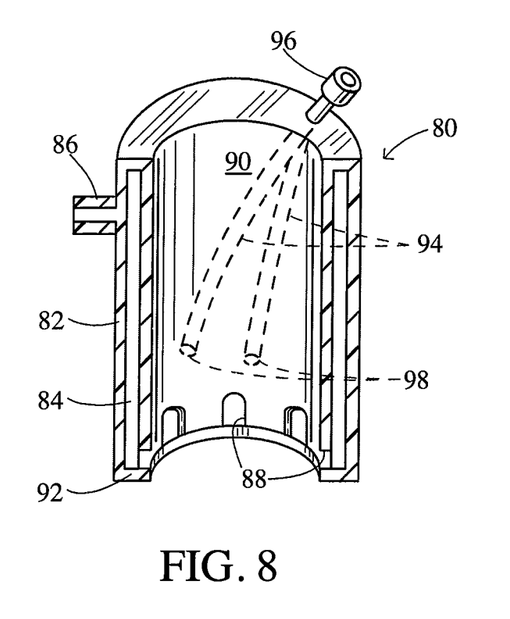
FIG. 8 is a schematic perspective view, partially in cross-section, of an additional sheath or surgical port device in accordance with the present invention.
Figure 9:
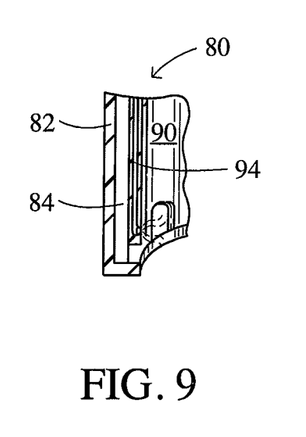
FIG. 9 is a partial cross-sectional view similar to FIG. 8 showing a detail of the sheath or port device of FIG. 8.

As illustrated in FIGS. 8 and 9, a sheath or port member 80 includes a tubular body member 82 that is at least partially hollow and is provided with one or more longitudinal channels 84 that extend from a connector 86 at a proximal end of the sheath or port member to one or more fluid inlets 88 disposed along an inner surface 90 of the body member at a distal end 92 thereof. In the case of multiple fluid inlets 88, the inlets are preferably angularly equispaced about the circumference of the body member 82. (Typically the port members described herein are cylindrical for purposes of evenly distributing stresses; however other cross-sectional shapes may be used.) Connector 86 receives a suction tube 87 extending from a suction source or vacuum pump (not illustrated) for evacuating irrigant and surgical detritus from a surgical site via inlets 88.

As further illustrated in FIGS. 8 and 9, sheath or port member 80 may be provided with one or more longitudinally extending optical fibers 94 that may be embedded in the wall of the body member 82. Optical fibers 94 are connectable via a coupling 96 to a light source (not illustrated) and extend to light outlets 98 disposed about the inner surface 90 preferably but not necessarily near distal end 92. The other port members disclosed herein may likewise be provided with suction and optical fiber illumination as in sheath or port member 80.

Another embodiment incorporates a protective sheath strategy into the minimally invasive access device to prevent unintended tissue damage to the tissue adjacent to the access device. This sheath can be an insert that is placed as a single use or reusable device into the access port or retractor that creates a barrier for vibratory transmission of energy through the walls of the access devices. In another embodiment the sheath is embedded in the access device as part of the design of the minimally invasive access device preventing vibratory transmission sufficient to cause unintended tissue damage.

Figures 10, 11:
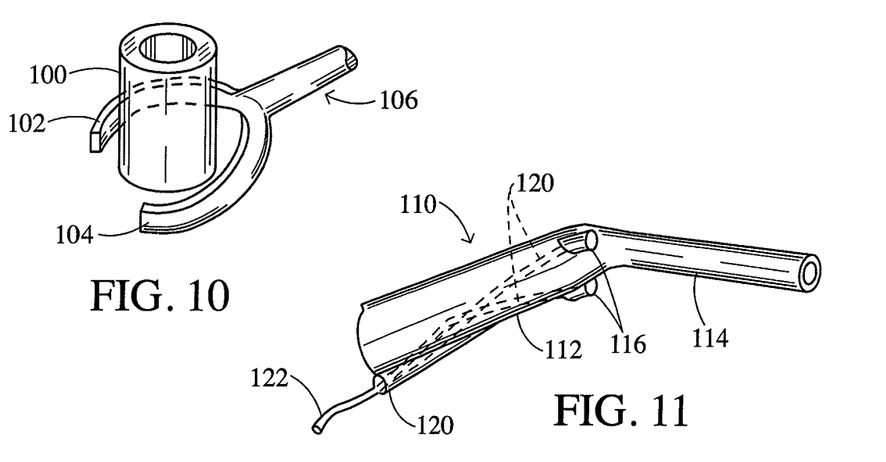
FIG. 10 is a schematic perspective view of a sheath or port device in accordance with the invention, in use with a surgical retractor.
FIG. 11 is a schematic perspective view, on a reduced scale, of another surgical instrument sheath in accordance with the invention.

As shown in FIG. 10, a tubular sheath or port member 100 is disposed between spaced or separated arms 102 and 104 of a surgical retractor 106. Sheath or port member 100 may take any form described herein, e.g., sheath or port member 20, 36, 50, or 80.

Another embodiment incorporates an endoscopic or illumination-providing device to improve visualization of the targeted treatment site delivered through the sheath. The combination of improved visualization of the treatment site while protecting all non-targeted tissue along the vibratory transmission path improve the safety of the device. In another embodiment the endoscopic or illumination-providing device is coupled with a light source that either exits the sheath at the extended portion of the handle so that it illuminates the field from above the retractor entry point. Or at the applicator tip. The light source is connected outside the surgical field. The improved visualization in combination with the protective aspect of the sheath reduces the potential for unintended tissue damage in minimally invasive surgery As depicted in FIG. 11, a sheath 110 having a large proximal end portion 112 and a smaller-diameter distal end portion 114 inclined relative thereto, is provided with one or more light emitters 116 at the distal end of the proximal end portion 112. Light emitters may be LEDs or may be the ends of optical fibers 118 extending to a coupling 120 that is connectable to a light source via an optical cable 122. In the case of LEDs the optical fibers 118 and cable 122 are replaced by electrical wiring extending to a source of electrical current.

Figure 12:
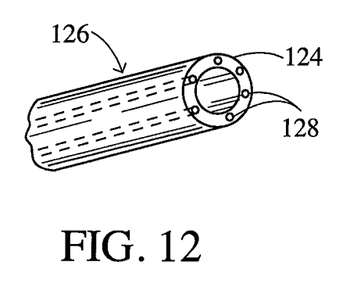
FIG. 12 is a schematic partial perspective view of a distal end portion of a further surgical instrument sheath in accordance with the invention.

As depicted in FIG. 12, the distal end 124 of a sheath 126 may be provided with one or more optical fiber outlet ports 128. These outlets 128 may include lenses for ensuring adequate illumination or light distribution.

In another preferred embodiment the protective sheath is mounted to the probe that transmits the vibratory energy to the treatment site along the shaft by means of spacers positioned at the nodal plane where vibration is at its lowest amplitude. This fixation method allows for maximum protection by the sheath along the transmission path allowing for avoidance of unintended tissue damage. The length of the sheath can be as short as an extension of the handle allowing for better hand placement by the surgeon without impeding visualization to as long as extending from the handle to the tip of the probe allowing protection up to the applicator tip at the treatment site. The application of the sheath mounting technique can be employed to enable curved probes that move the holding of the probe outside the visual field while still being able to grasp a place along the transmission pathway of the probe that absent the sheath would cause unintended tissue damage to the surgeons hands.

Figure 13:
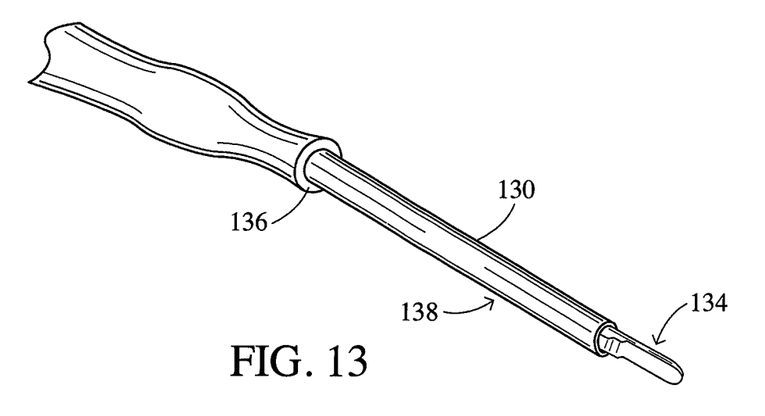
FIG. 13 is a perspective view of an ultrasonic bone cutting blade and associated sheath in accordance with a feature of the present invention.
Figure 14:
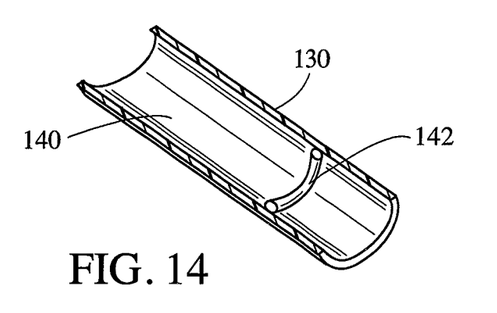
FIG. 14 is a cut-away perspective view of a distal end of a sheath like that of FIG. 13.
Figure 15:
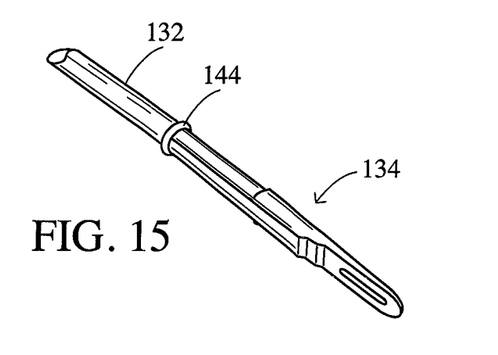
FIGS. 15-17 are perspective views of the distal end of an ultrasonic bone cutting blade, showing alternative features of the present invention.
Figure 16:
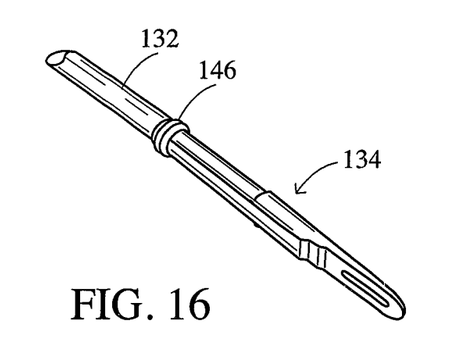
Figure 17:
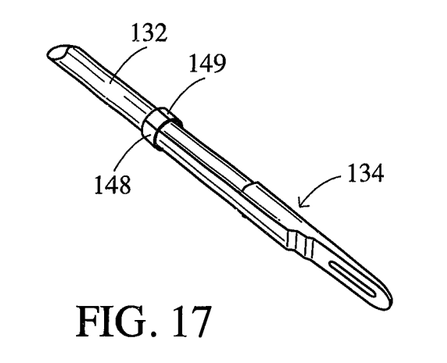

As shown in FIG. 13, a sheath 130 may be supported on a shaft or horn 132 (see FIGS. 15-17) of an ultrasonically vibratable probe 134 at nodal planes or regions 136 and 138. As shown in FIG. 14, sheath 130 may be provided along an internal surface 140 with an inwardly projecting annular rib 142 that is engageable with probe horn 132. Alternatively, as shown in FIG. 15, probe horn 134 may be provided with an outward projecting annular rib 144 preferably located at a nodal plane or region 138. A shown in FIGS. 16 and 17, probe shaft or horn 132 may be provided with a molded rib 146 or a rib 148 with longitudinal grooves 149 (for enabling longitudinal fluid transmission along the probe shaft).

Another embodiment incorporates the ability to transmit light through the sheath to emit at the end of the sheath closest to the applicator tip illuminating the target treatment area and improving visualization. In another embodiment the light source can exit the sheath at the extended portion of the handle so that it illuminates the field from above the retractor entry point. The light source is connected outside the surgical field. The improved visualization in combination with the protective aspect of the sheath reduces the potential for unintended tissue damage in minimally invasive surgery.

In another embodiment a protective sheath is used with an ultrasonic bone scalpel in a minimally invasive approach. The protective sheath protects the ultrasonic vibratory elements along the transmission path in such a way that the probe can be held outside of the field of vision of the minimally invasive access port so that an ultrasonic bone scalpel can be delivered to the targeted treatment site. The protective sheath may extend down the length of the transmission path to further prevent unintended tissue damage. The sheath can incorporate a light feature that illuminates the targeted treatment area. The sheath can incorporate either suction or irrigation or both to manage thermal build up, or remove debris from the targeted treatment area. The combination of the protective sheath and the ultrasonic bone scalpel create a device that can be applied to hard tissue at the applicator tip (bone scalpel) without damaging soft tissue below or adjacent to the targeted treatment site.

Figure 18:
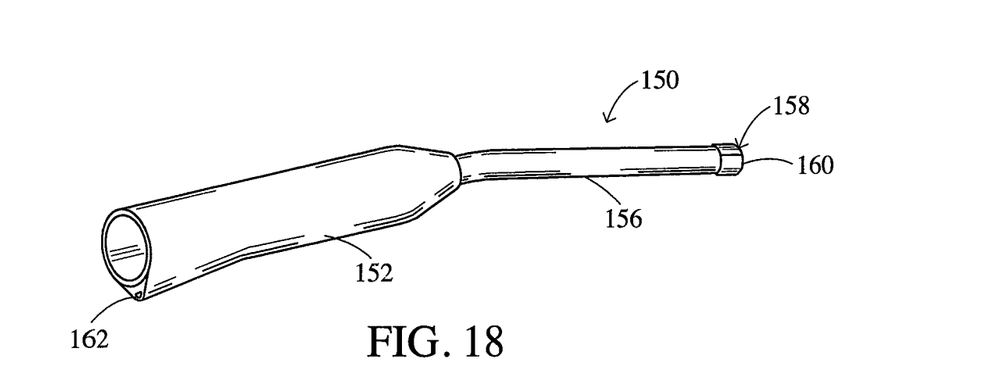
FIG. 18 is a perspective view of another sheath in accordance with the present invention.

As shown in FIG. 18, a sheath 150 for an ultrasonic bone cutting instrument or probe 152 or other instrument has a large proximal end portion 154 and a smaller-diameter distal end portion 156 inclined relative thereto and is provided at a distal end of small-diameter proximal portion 156 with a translucent or transparent annular end piece 158 serving as an illuminator. End piece 158 may be provided with a reflective coating (not separately enumerated) that is selectively applied for shaping the distribution or pattern of electromagnetic radiation emitted from the end piece. For instance, the coating may be applied to permit light to exit only from a tip or distal end face 160 of the sheath 150.

Typically, a fiber optic light transmission path extends to end piece 158 from a coupling 162 at the proximal end of proximal sheath end portion 154.

Typically, the instrument used in conjunction with sheath 150 (e.g., bone cutting probe 152) has a axial channel or bore for delivering irrigant to a blade or other end effector or operative probe head 164.

Figures 19, 20:
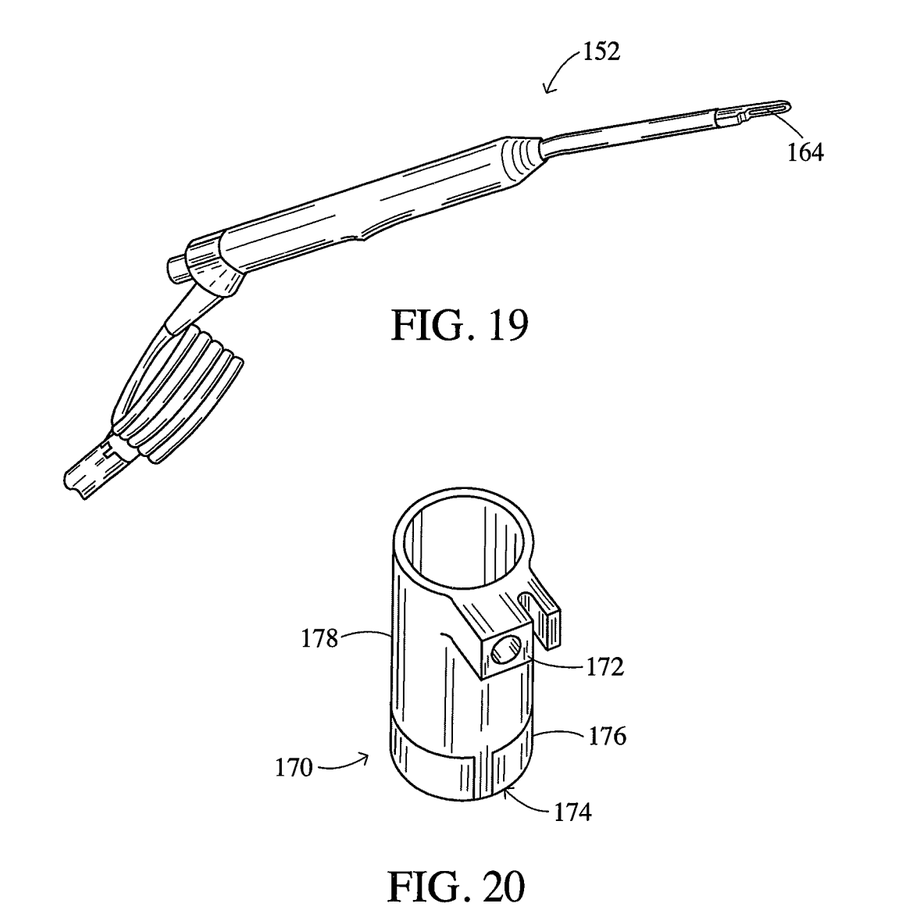
FIG. 19 is a perspective view of an ultrasonic surgical instrument utilizable with the sheath of FIG. 18.
FIG. 20 is a perspective view of yet another sheath or port device pursuant to the invention.

FIG. 20 illustrates a port member 170 in the form of a tubular member having a light coupling 172 at a proximal end and an annular translucent or transparent illuminator piece 174 at a distal end. Illuminator piece 174 is provided along an outer surface (not separately designated) with a reflective coating 176 for increasing luminosity in an area within the tubular port member 170. Optical fibers extend within a body portion 178 of the tubular port member from coupling 172 to illuminator piece 174. Coating 176 may be selectively applied controlling light distribution, with light shining everywhere that is not painted.

Figure 21:
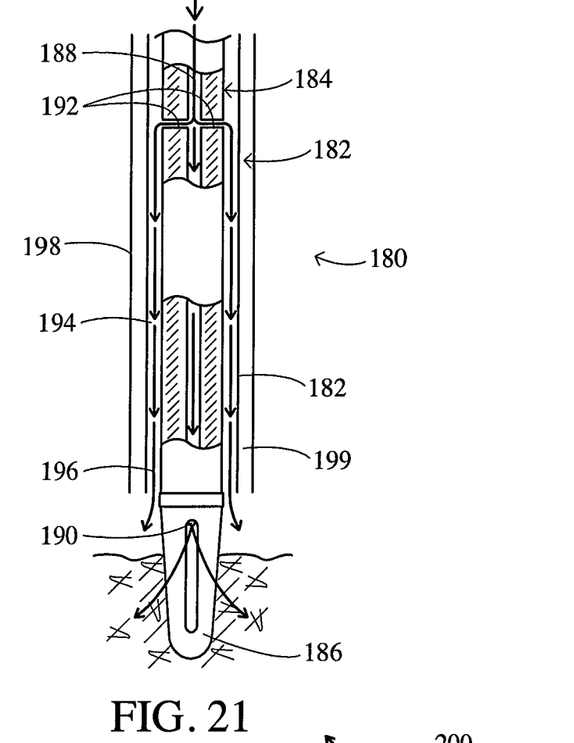
FIG. 21 is a schematic longitudinal cross-sectional view of another surgical instrument assembly pursuant to the invention.

FIG. 21 shows an ultrasonic instrument assembly 180 including a sheath 182 and a probe shaft 184 extending longitudinally through the sheath. The probe shaft 184 is provided at a distal end with an operative head 186 such as a bone-cutting blade. Probe shaft 184 is formed with a longitudinal channel or bore 188 extending to a outlet port 190 in head 186. Shaft or horn 184 is further provided with at least one duct 192 extending between channel or bore 188 on an inner side and a space 194 between sheath 182 and probe shaft 184 on an outer side. Instrument assembly 180 is used to perform a surgical operation on selected organic tissues of a patient, where the operative head 186 is positioned in effective engagement with the tissues during the using of the instrument. Liquid irrigant is directed through channel or bore 188 to outlet 190 during at least an initial phase of the procedure. When and if the outlet 190 becomes blocked or occluded with tissue, liquid irrigant is automatically directed from channel or bore 188 and through duct(s) 192 to space 194 and out or the space 194 at 196. A further sheath may be disposed coaxially with and outside of sheath 182 to provide a further annular channel 199 for suction. Arrows (not designated) in FIG. 21 show the two alternative flow paths as described.

Figure 22:
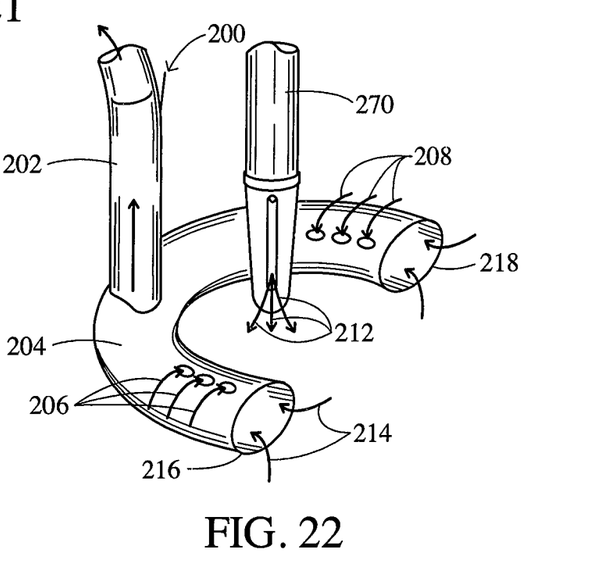
FIG. 22 is a schematic perspective of a suction device disposable inside, or in place of, a retractor or port device as described herein.

FIG. 22 shows a suction device 200 utilizable in a minimally invasive spinal or orthopedic surgical procedure. Suction device 200 has a longitudinal shaft 202 and a U-shaped, C-shape, or annular suction head member 204 at a distal end of the shaft portion 202. Suction head 204 is provided with an array of suction inlets 206. Shaft member 202 is operative connectable at a proximal end to a suction source (not shown) for evacuating irrigant and organic debris from a surgical site through inlets 206. Suction member may be disposed inside a retractor or may itself function as a retractor. In the latter case, the suction head 204 is best configured as an annular or ring shaped piece. Arrows 208 indicate fluid flow paths extending through inlets 206. An ultrasonic bone cutting instrument is depicted at 210, with arrows 212 indicating fluid flow from that instrument.

As indicated by fluid flow arrows 214, ends 216 and 218 of a U- or C-shaped suction head 204 may be open for liquid evacuation.

What is claimed is:

1. A surgical method comprising:
    providing a tubular member having an annular translucent or transparent element at one end, said translucent or transparent element defining an enclosed space at said one end of said tubular member and being provided along an outer surface with a coating of a light reflective material;
    forming an opening or incision in tissues of a patient;
    inserting said tubular member into said opening or incision so that said tubular member maintains said opening or incision in an open configuration;
    directing visible light energy along a fiber optic guide in a sidewall of said tubular member to said annular translucent or transparent element;
    reflecting said visible light energy from said reflective material so that light shines into said enclosed space; and
    performing an operation on tissues in said enclosed space during the directing of said light energy.

2. The method defined in claim 1 wherein the performing of said operation includes inserting a distal end of an ultrasonic surgical instrument into said area and ultrasonically vibrating an operative head of said instrument during an engagement thereof with said tissues.

* * * * *